US00RE40215E

(19) United States
(12) Reissued Patent
Cummings et al.

(10) Patent Number: US RE40,215 E
(45) Date of Reissued Patent: Apr. 8, 2008

(54) STABILIZER ATHLETIC SHOES

(76) Inventors: William G. Cummings, 322 Hilltop Rd., Mahush, NJ (US) 07430; Jay G. Levine, 5 Walnut St., New City, NY (US) 10956

(21) Appl. No.: 10/974,957

(22) Filed: Oct. 27, 2004

Related U.S. Patent Documents

Reissue of:
(64) Patent No.: 6,474,006
Issued: Nov. 5, 2002
Appl. No.: 09/617,732
Filed: Jul. 17, 2000

(51) Int. Cl.
*A61F 5/14* (2006.01)
*A43B 7/14* (2006.01)

(52) U.S. Cl. ..... 36/142; 36/88; 36/25 R; 36/144

(58) Field of Classification Search ..... 36/25 R, 36/142, 143, 144, 103, 127, 88, 92
See application file for complete search history.

(56) References Cited

U.S. PATENT DOCUMENTS 211,017 A * 12/1878 Dyer ..... 36/69
912,862 A * 2/1909 Lendgren ..... 36/69
2,179,942 A * 11/1939 Lyne ..... 36/127
2,616,190 A * 11/1952 Darby ..... 36/144
2,847,769 A * 8/1958 Schlesinger ..... 36/127
3,218,734 A * 11/1965 O'Brien ..... 36/133
4,073,075 A * 2/1978 O'Brien ..... 36/127
4,118,034 A * 10/1978 O'Brien ..... 473/217
4,402,146 A * 9/1983 Parracho et al. ..... 36/129
4,484,397 A * 11/1984 Curley, Jr. ..... 36/92
4,620,376 A * 11/1986 Talarico, II ..... 36/103
4,685,227 A * 8/1987 Simmons ..... 36/127
4,748,753 A * 6/1988 Ju ..... 36/127
4,866,861 A * 9/1989 Noone ..... 36/127
5,345,701 A * 9/1994 Smith ..... 36/144
5,448,839 A * 9/1995 Blissett et al. ..... 36/25 R

* cited by examiner

*Primary Examiner*—Marie Patterson

(57) ABSTRACT

An athletic shoe is provided which contributes a dynamic stability of the shoe during several athletic activities. The athletic shoe comprises a tapered lateral wedge section and may further include a lateral heel stabilizer, a medial heel wedge and a tapered lateral forefoot section.

10 Claims, 3 Drawing Sheets

STABILIZER ATHLETIC SHOES

Matter enclosed in heavy brackets [ ] appears in the original patent but forms no part of this reissue specification; matter printed in italics indicates the additions made by reissue.

FIELD OF THE INVENTION

This invention relates generally to athletic shoes and particularly to stabilizer athletic shoes for persons engaged in athletic activities. More specifically, this invention relates to an improved athletic shoes construction which incorporate features designed to increase foot and ankle stability during various athletic activities in order to decrease muscle fatigue, enhance performance and minimize injuries.

BACKGROUND OF THE INVENTION

Various athletic shoes are presently being marketed for different activities such as running, tennis, basketball, racqetball and golf. These shoes are designed to prevent, or at least minimize injuries caused by lateral foot ankle instability during such activities. Current athletic shoes do not adequately guard against injuries caused by all type of athletic activities, including those activities which involve side-to-side jumping motions. These activities have greater tendency for lateral foot ankle instability, and hence injury in the foot and/or ankle.

U.S. Pat. No. 3,738,373, issued Jun. 12, 1973 descries an athletic shoe which incorporates a flexible wedge mounted therein which extends completely to the rear edge of the heel thereby providing maximum "cushion".

An earlier patent, U.S. Pat. No. 2,847,769, issued Aug. 19, 1958 discloses shoes for golfers which are designed to compel a golfer to automatically assume the correct golf stance.

Other athletic shoes incorporate air-cushioning means, usually in the heels, for absorbing the impact experienced during said activities.

So far as it is know, there is no single pair of athletic shoes which adequately affords the desired degree of protection and guards against injuries resulting from foot instability during athletic activities of the type hereinbefore mentioned. This is largely because the foot-angle structure is complex and includes numerous joint axis with different movements and displacements in response to varying impacts and positions. Thus, the design of an athletic shoe which can protect against the different possible injuries resulting from a variety of athletic activities must take into consideration such factors as supination, pronation, dorsiflexion, plantarflexion, abduction, and adduction which occur at the foot-ankle joint during said sports activities. Accordingly, there is need for a single athletic shoe which is designed to afford maximum benefits for those engaged in various athletic activities in which foot-ankle injuries are matter of common experiences.

It is therefore an object of the present invention to provide an athletic shoe which is designed to afford maximum protection against injuries resulting from sports activities involving jumping and side-to-side motions such as, e.g., running, jumping, basketball, tennis and racquetball.

It is a further object of this invention to provide athletes with athletic shoes which incorporate features that counter the adverse effects of such factors as supination, pronation, dorsiflexion, plantarflexion, abduction and adduction experienced by athletes during several athletic activities.

The foregoing and other objects of this invention will become more apparent from the following detailed description and accompanying drawings.

SUMMARY OF THE INVENTION

In accordance with the present invention an athletic shoe is provided which, because of its unique construction, assures dynamic foot stability, reduces lateral ankle instability and alleviate foot fatigue which often results from athletic activities such as jogging, running, tennis, basketball, jumping and even weight lifting exercises. In one embodiment, the athletic shoe comprises heel and a sole having a rear foot portion and a forefoot portion which has a medial section and a lateral section. The forefoot portion has a lateral wedge conformally affixed thereto or formed, integrally therewith, said lateral wedge member being tapered from the medial section toward the lateral mid portion of the forefoot.

In a second embodiment, the shoe is similar to the first embodiment and further includes a lateral heel stabilizer conformally attached to the heel counter, a medial heel wedge spanning the length and width of the shoe heel, and a tapered lateral forefoot member attached to the bottom sole of the shoe.

BRIEF DESCRIPTION OF THE DRAWINGS

In the drawings, wherein the same reference numerals in the different figures designate like parts:

FIGS. 1-7 illustrate the left shoe, it being understood that the right shoe is similar in construction with the specific features being located on opposite side of the shoe.

DETAILED DESCRIPTION OF DIFFERENT EMBODIMENTS THE INVENTION

Figure 1:
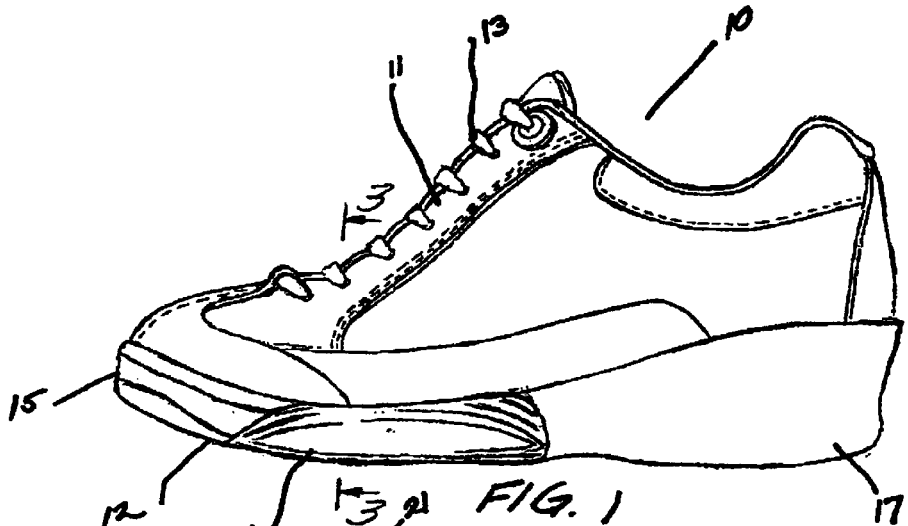
FIG. 1 is a side elevational partly perspective view of an athletic shoe incorporating a lateral forefoot wedge in accordance with one embodiment of the present invention.
Figure 2:
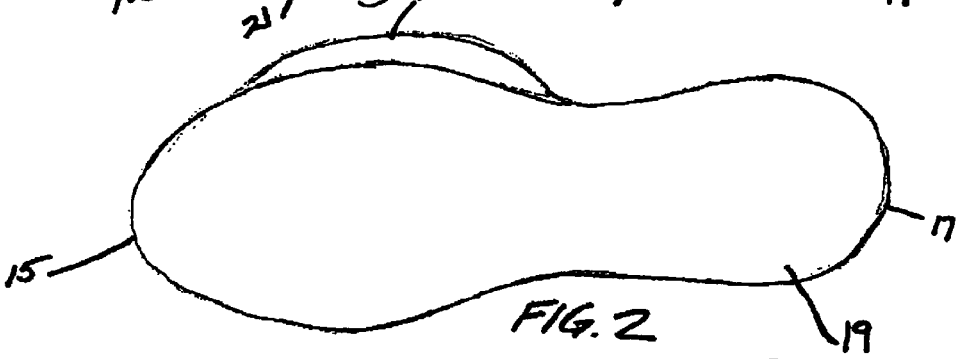
FIG. 2 is a bottom view of the shoe shown in FIG. 1.
Figure 3:
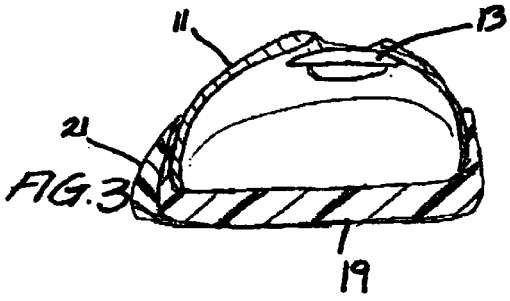
FIG. 3 is a sectional view taken along the line 3-3 of FIG. 1.

Referring to FIGS. 1-3, there is shown, in FIG. 1, a sport shoe 10 having a flexible top portion 11 mounted on top of the shoe sole 12 and is tied around the top portion 11 by the shoe lace 13. The sole 12 extends from the toe portion 15 to the heel portion 17 which may be rigid or semi-rigid in construction. The bottom or outsole 19 (see FIG. 2) may be ribbed, grooved or patterned as desired. For the purposes of use in some sports, the heel may be cushioned, or rendered resilient and capable of absorbent shocks upon impact by including air ducts, air pellets or spring means between the heel and the sole. Such constructions are well known in the prior art. For the purposes of this invention, in the embodiment shown in FIGS. 1-3, the shoe is provided with an external lateral forefoot stabilizer 21 which is formed as an integral part of the shoe conformally contouring the lateral forefoot portion of the shoe. The lateral forefoot stabilizer 21 is preferably about ⅛ to about ¼ inch thick and is attached to the edge of the sole, with its thickness increasing gradually toward the lateral side where it is at its greatest thickness. The lateral forefoot stabilizer 21 extends a distance of from about 2 to about 4 inches, from the middle toward the toe portion 15, thus extending from the $5^{th}$ toe proximal to the $5^{th}$ metatarsal base. The lateral forefoot stabilizer 21 may be made of the same material used in forming the shoes, generally hard rubber, neoprene or a plastic. such as a copolymer of ethylene and vinyl acetate (EVA). The provision of the lateral forefoot wedge 21 will accomplish two goals, i.e., locking the metatarsal joint at propulsive phase of gait thus producing a stronger lever arm which results in increased push-off power. In addition, it decreases lateral ankle instability in the types of sport activities which require excessive medial to lateral movements.

Figure 4:
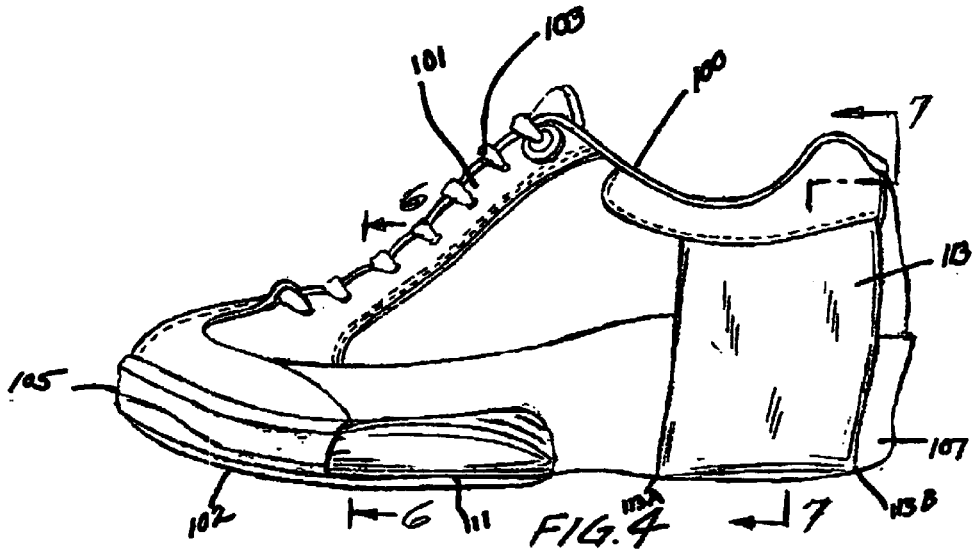
FIG. 4 is a side elevational, partly perspective view of an athletic shoe made according to another embodiment of this invention.

Referring now to the embodiment of this invention illustrated in FIGS. 4-7, there is shown, in FIG. 4, an athletic shoe generally designated as 100 having a flexible top portion 101 mounted on top of the shoe sole 102 and tied around the top foot portion 101 by the shoe lace 103. The sole 102 extends from the toe portion 105 to the heel portion 107 which may be rigid or semi-rigid in construction. The bottom shoe sole 109 may be ribbed, grooved or patterned as desired. As in the embodiment shown in FIGS. 1-3, the heel may be cushioned or rendered resilient so as to withstand the impacts experienced by athletes during jumping, running, jogging and other foot-to-ground impact producing activities.

In this embodiment of the invention, and as seen in FIGS. 4-7, the shoe 100 is provided with an external lateral forefoot stabilizer 111, a lateral heel stabilizer 113, a medial heel wedge 115 and a bottom forefoot wedge 117, all of which contribute to the rigidity and dynamic stability of the shoe.

The lateral forefoot stabilizer 111 serves a similar function and purpose as the lateral forefoot stabilizer 21 described in conjunction with FIG. 1. The lateral forefoot stabilizer 111 is made of plastic or rubber, the same as the shoe, is disposed proximal to the $5^{th}$ metatarsal, is conformably attached laterally to the shoe, extending about 1 to 3 inches from the middle toward the toe portion 105. The provision of the lateral forefoot stabilizer 111 guards against lateral instability of the foot and the ankle (strains and sprains) and excessive frontal plane motions.

The lateral heel stabilizer 113 is a piece of rubber or plastic (EVA) which is about 2 to 3 inches wide, about 2-3 inches high (depending on the height of the shoe) and is about ⅛ to ¼ inch thick. The lateral heel stabilizer 113 is attached to the rear exterior of the shoe above the heel 107 extending from the proximal end 113B to the distal end 113A near the top of the shoe, thus adding firm support to the lateral heel and reducing lateral ankle sprains experienced in sports such as basketball and tennis. It also provides added stability and push-off power in such activity as weight lifting.

Figure 5:
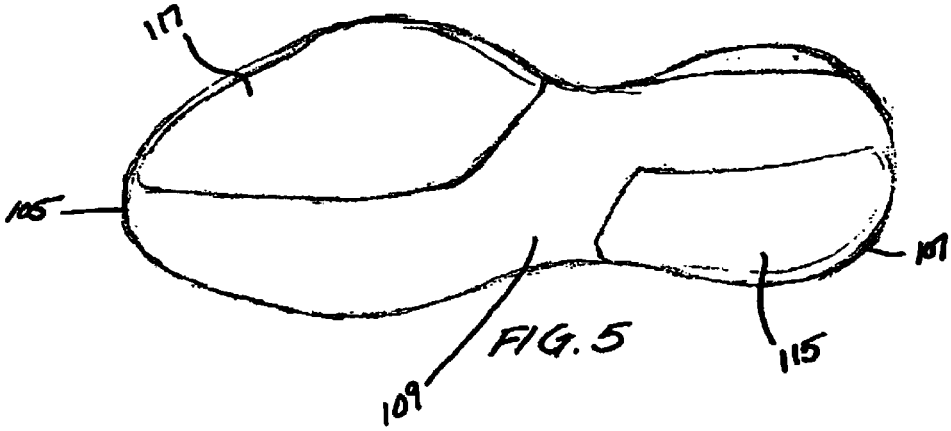
FIG. 5 is a bottom view of the shoe shown in FIG. 4.
Figure 6:
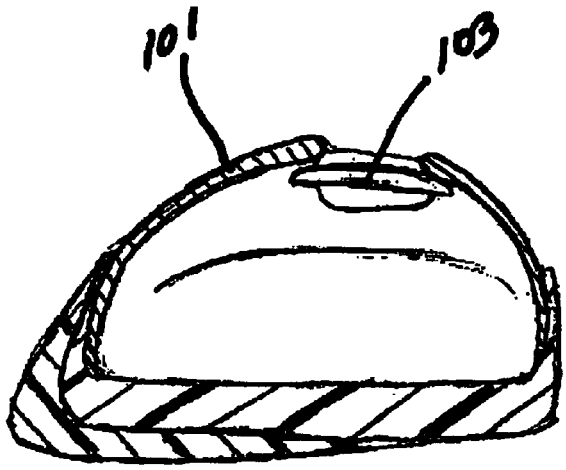
FIG. 6 is a view taken along the line 6-6 of FIG. 4.
Figure 7:
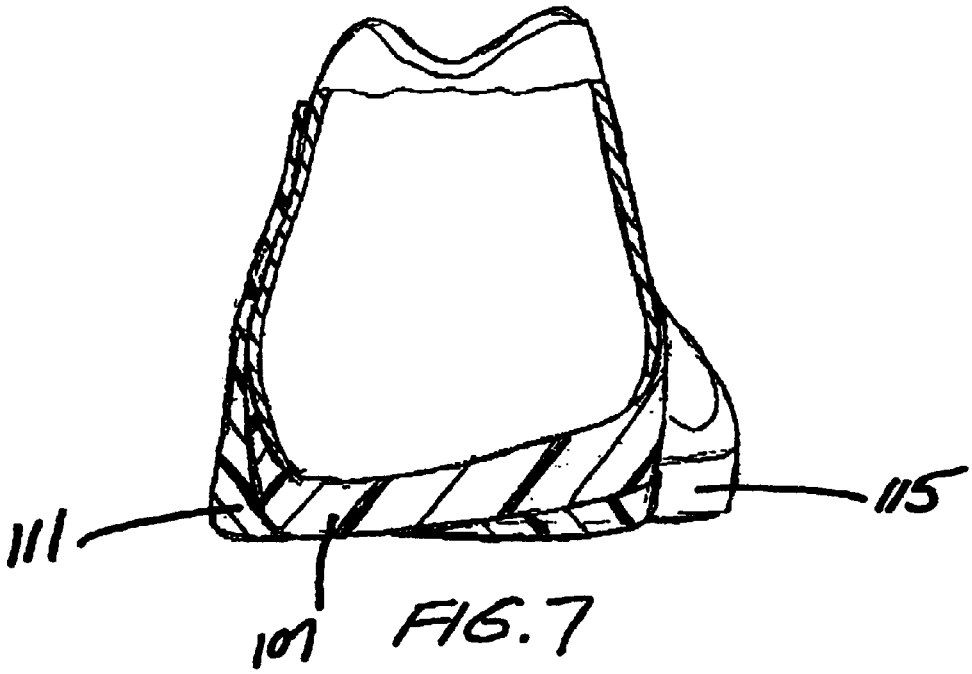
FIG. 7 is a view taken along the line 7-7 of FIG. 4.

The athletic shoe 100 also comprises a medial heel wedge 115, which may be ribbed, grooved or patterned as desired, and it is incorporated into the heel structure and/or affixed thereto at about 2 to 5 degrees relative to the ground. As shown in FIG. 5, the wedge 115 spans the entire length and approximately ½ of the width of the heel with the highest part of the wedge being at the medial inner heel. Thus, the rear of the athletic shoe will have a mild tilt outward, i.e., away from the body. The incorporation of the medial heel wedge in the athletic shoe as aforesaid limits the pronation and inversion of the foot as the heel stricks the ground. It is a matter of common experience that most overuse syndrome, including plantar facilities, posterior tibial medial tendonitis, knee and lower back pain are due to, or exacerbated by over pronation or an exaggerated inward rolling of the foot. By providing a medial heel wedge as herein described, pronation will be effectively reduced, foot and leg fatigue will be alleviated and foot stability is increased, all of which contribute to dynamic stability during athletic performance.

Referring again to FIG. 5, the shoe 100 is provided, at its bottom, with a tapered lateral forefoot wedge 117 conformally contoured to the forefoot, which is approximately ⅛ to 3/16 inch thick, and is tapered medial to lateral from the middle forefoot, with its thickest part being at the lateral side. In orthopedic jargon, the forefoot wedge 117 extends from the $5^{th}$ toe proximal to the $5^{th}$ metatarsal base. As previously mentioned, the inclusion of the lateral foot wedge in the shoe results in a more vertical push-off power and decreases lateral ankle stability whenever excessive medial to lateral movements are encountered.

It can be appreciated from the foregoing description of the different embodiments of the novel athletic shoes that several changes and modifications may be made in the structure of the shoe which are suggested by the description and the drawings herein. Such changes and modifications are nevertheless within the scope of the present invention.

What is claimed is:

1. A stabilizer athletic shoe comprising a sole having a bottom portion, a forefoot having a top portion, a rearfoot portion, an edge and a heel portion, said forefoot portion having a medial part and a lateral part, an external lateral foot stabilizer attached to the edge of said sole, a bottom forefoot wedge member attached to the bottom of said sole, a medial heel wedge having a bottom portion wherein said heel wedge spans substantially the entire length, and about one-half the width of said heel, and a heel stabilizer extending from the bottom portion of said heel to the top of the rearfoot portion.

2. A stabilizer athletic shoe as in claim 1 wherein said external lateral foot stabilizer is from about ⅛ to about ¼ inch thick, with the thickness increasing from said medial part to said lateral part of said forefoot portion.

3. A stabilizer athletic shoe as in claim 1 wherein said bottom forefoot wedge member and said lateral foot stabilizer partly overlap one another.

4. A stabilizer athletic shoe as in claim 2 wherein said bottom forefoot wedge member and said lateral foot stabilizer partly overlap one another.

*5. A stabilizer athletic shoe comprising a sole having a bottom portion, a forefoot having a top portion, a rear foot portion, an edge and a heel portion, said forefoot portion having a medial part and a lateral part, and a lateral foot stabilizer integral with and conformally contouring the edge of said sole.*

*6. A stabilizer athletic shoe as in claim 5 wherein said lateral foot stabilizer is from about ⅛ to about ¼ inch thick, with the thickness increasing from said medial part to said lateral part of said forefoot portion.*

*7. A stabilizer athletic shoe as in claim 5 further including a forefoot wedge member.*

*8. A stabilizer athletic shoe as in claim 7 wherein said forefoot wedge member and said lateral foot stabilizer partly overlap each other.*

*9. A stabilizer athletic shoe as in claim 7 wherein said lateral foot stabilizer is from about ⅛ to about ¼ inch thick, with the thickness increasing from said medial part of said lateral part of said forefoot portion.*

*10. A stabilizer athletic shoe as in claim 8 wherein said lateral foot stabilizer is from about ⅛ to about ¼ inch thick, with the thickness increasing from said medial part to said lateral part of said forefoot portion.*

* * * * *